United States Patent
Shimizu et al.

[11] Patent Number: 5,861,384
[45] Date of Patent: Jan. 19, 1999

[54] IMMUNOSUPPRESSIVE-ACTIVITY POTENTIATING COMPOSITIONS

[75] Inventors: Nobuyoshi Shimizu; Motoi Aoe; Tetsunobu Udaka, all of Okayama; Toshiharu Tsuboi; Ken-ichi Yoshida, both of Osaka, all of Japan

[73] Assignee: Senju Pharmaceutical Co., Ltd., Osaka, Japan

[21] Appl. No.: 785,740

[22] Filed: Jan. 17, 1997

[30] Foreign Application Priority Data

Jan. 17, 1996 [JP] Japan .................................. 8-005584

[51] Int. Cl.⁶ .................................. A61K 21/665
[52] U.S. Cl. .................................. 514/100
[58] Field of Search ........................ 514/100

[56] References Cited

U.S. PATENT DOCUMENTS

| | | |
|---|---|---|
| 4,564,686 | 1/1986 | Ogata . |
| 4,888,329 | 12/1989 | Ogata et al. . |
| 4,914,197 | 4/1990 | Yamamoto et al. . |
| 4,948,786 | 8/1990 | Shimamoto et al. . |

FOREIGN PATENT DOCUMENTS

| | | |
|---|---|---|
| 0127471 | 12/1984 | European Pat. Off. . |
| 0616809 | 9/1994 | European Pat. Off. . |
| 0643969 | 3/1995 | European Pat. Off. . |
| 27044/89 | 5/1989 | Japan . |
| 90/03793 | 4/1990 | WIPO . |

OTHER PUBLICATIONS

Transplant. Proc., vol. 25, No. 1, 1993, pp. 610–611, XP000653615, D. Slakey et al.: "Ascorbic acid and alpha–tocopherol prolong rat cardiac allograft survival".

*Primary Examiner*—Raymond Henley, III
*Attorney, Agent, or Firm*—Merchant, Gould, Smith, Edell, Welter & Schmidt

[57] ABSTRACT

According to the present invention, there are provided immunosuppressive-activity potentiating compositions which comprise a phosphoric acid diester compound represented by the following formula [I]:

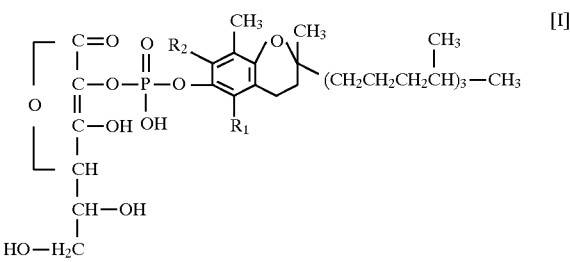

($R_1$ and $R_2$ are the same or different and represent individually a hydrogen atom or methyl group) or its pharmacologically acceptable salt, and the immunosuppressive-activity potentiating compositions can suppress effectively acute rejection after transplantation.

9 Claims, 1 Drawing Sheet

IMMUNOSUPPRESSIVE-ACTIVITY POTENTIATING COMPOSITIONS

BACKGROUND OF THE INVENTION

The present invention relates to useful immunosuppressive-activity potentiating compositions. In more particular, this invention is concerned with immunosuppressive-activity potentiating compositions which comprise a phosphoric acid diester compound of ascorbic acid with tocopherol or its pharmacologically acceptable salt.

The transplantation surgery is one of the rapidly developed medical techniques. This is because tremendous efforts have been made in the development of immunosuppressive drugs, progress in the surgical procedures and promotion of counter-measures against infection to thereby improve the treatment performances, and the transplantation surgery surpassed the experimental stage and has nowadays turned into an established treatment technique in common use.

In order to secure the prevention of organ graft rejection after the transplantation surgery, however, it in fact is necessary and indispensable to give patients immunosuppressive drugs at increased doses, as has actually been the case with human organ transplantation surgeries.

In addition, the immunosuppressive compositions are administered to patients in the treatment of autoimmune disorders.

The immunosuppressive drugs, especially cyclosporine A and the like, which are used in the human organ transplantation and treatment of autoimmune disorders, cause the incidence of such serious side effects as nephrotic disturbances, increase in blood pressure, rhabdomyolysis, hemolytic uremia syndrome and dysbolism, and have therefore been deemed quite controversial from a clinical point of view. As a result that decreases in their doses have been considered of utmost importance.

In permitting the immunosuppressive drugs to separate their efficacy from side effects, it is necessary to avoid the overdose of such drugs exhibiting immunosuppressive activity, while it is thought of significance to search for a supplementary or prosthetic molecule which could show immunosuppressive-activity potentiating property as well as enhanced degrees of safety and efficacy.

In view of the status quo that there has been so far available no drug which can act as an immunosuppression potentiating, prosthetic molecule, a strong demand has been existing for the development of an efficient immunosuppressive-activity potentiating composition.

SUMMARY OF THE INVENTION

Under these circumstance, the present inventors conducted extensive research work while searching for an excellent immunosuppressive-activity potentiating composition, and as a result, found that a kind of phophoric acid diester compounds can be expected to act as an immunosuppressive-activity potentiating composition, leading to completion of the present invention.

Thus, the present invention relates to:

(1) Immunnosuppressive-activity potentiating compostions which comprise a phosphoric acid diester compound represented by the following formula [I]:

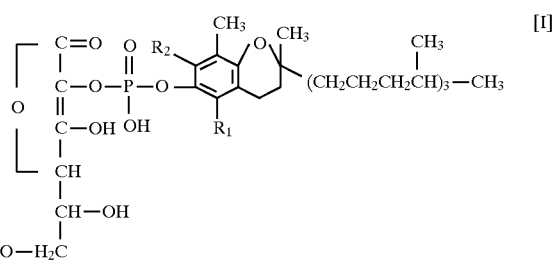

($R_1$ and $R_2$ are the same or different and represent individually a hydrogen atom or methyl group) or its pharmacologically acceptable salt, and (2) An immunosuppressive-activity potentiating composition as described in the item (1), wherein said immunosuppressive activity is the immunosuppressive activity elicited by cyclosphorine.

DESCRIPTION OF THE PREFERRED EMBODIMENTS

Figure 1:
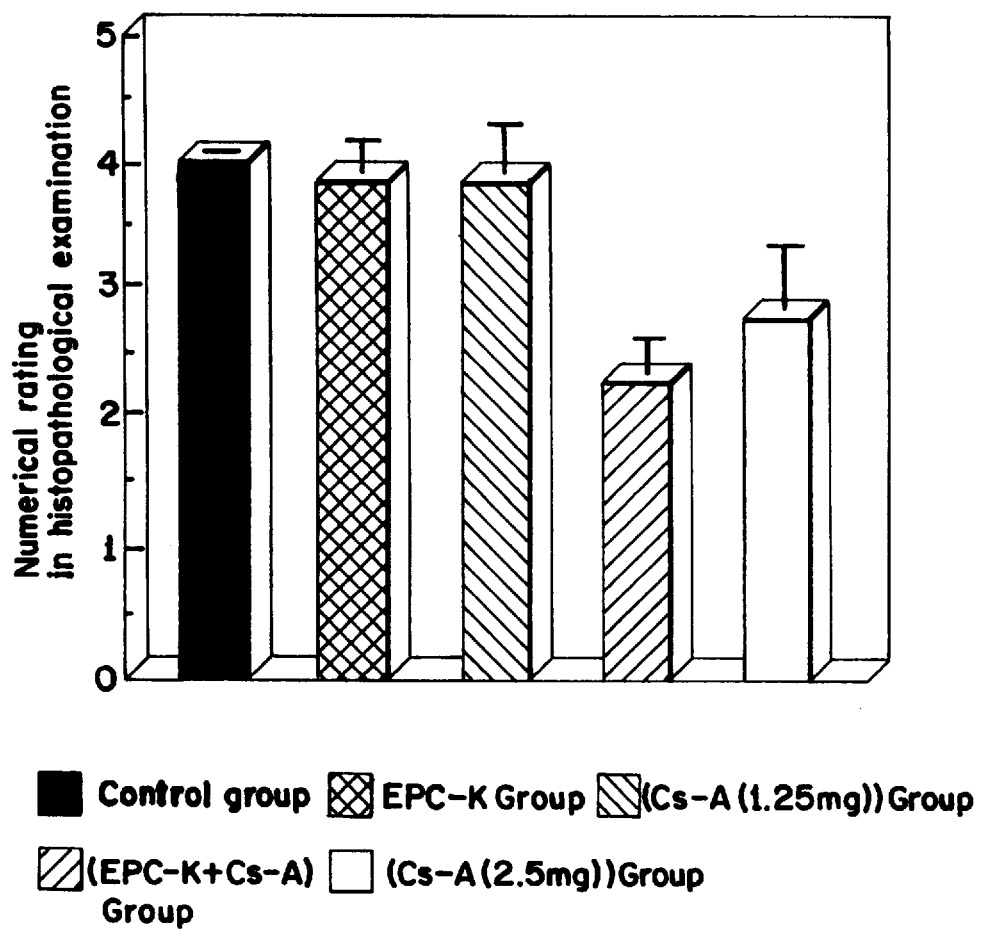
FIG. 1 is a graph comparing acute refection results after lung transplantation.

The term "immuno-suppressive-activity potentiating composition" throughout the present specification is understood to designate any immunosuppressive-activity potentiating compositions, which after being applied solely can elicit their potential activities, and any immunosuppressive-activity potentiating compositions, which can exhibit their activities when used in combination with immunosuppressive drugs.

The Present Compounds which are used as an immunosuppressive-activity potentiating composition of this invention can be synthesized in accordance with the procedures as described for example in the Official Gazettes of Japanese Unexamined Patent Publication Nos. 44478/1990 and 205091/1987, or those similar thereto.

The Present Compounds, which are usable in the immuno-suppressive-activity potentiating compositions according to this invention, have already been known to find widened application as various drugs or physiologically active substances, such as anti-cataract agents, prophylactic and therapeutic agents against menopausal disturbances and cosmetic showing skin-beautifying activity (Japanese Unexamined Patent Publication No. 44478/1990), anti-inflammatory agents (Japanese Unexamined Patent Publication No. 27044/1989) and anti-ulcer agents (Japanese Unexamined Patent Publication No. 270626/1988) as well as prophylactic and therapeutic agents against ischemic organic disturbances (Japanese Unexamined Patent Publication No. 111722/1990). Nevertheless, the Present Compounds have not yet been known to be of use as an immunosuppressive-activity potentiating agent.

The Present Compounds, which are usable in the immunosuppressive-activity potentiating compositions of this invention, can suitably be used for the purpose of this invention in the form of either a free acid or its pharmacologically acceptable salt. Such pharmacologically acceptable salt may be exemplified, for example, by alkali metal salts, such as sodium and potassium salts, and alkaline earth metal salts, such as calcium and magnesium salts, and any salts other than those can also suitably be employed, as long as they are pharmacologically acceptable.

The immunosuppressive-activity potentiating compositions of the present invention can also be incorporated with one, or two or more, of the Present Compounds, as the purpose and need may require.

The Present Compounds which are usable in the immunosuppressive-activity potentiating compositions of this invention, show extremely lowered toxicity and improved safety, and can therefore be utilized for the purpose of this invention, as is evidenced by the fact that potassium diphosphate of L-ascorbic acid-DL-α-tocopherol (or a compound of the formula [I] where $R_1$ is a methyl group and $R_2$ is a methyl group; hereinafter referred to briefly as "EPC-K") shows $LD_{50}$ values of 5 g/kg (in rats) when given orally and not less than 100 mg/kg (in rats) when injected intravenously.

The immunosuppressive-activity potentiating compositions of the present invention can be incorporated with other immunosuppressive-activity potentiating drugs and/or any ingredients which produce different efficacies, unless they are contradictory to the purpose of this invention.

The immunosuppressive-activity potentiating compositions of the present invention are suitably applied orally or parenterally (for example through intravenous injection, hypodermic injection, intramuscular injection and drip). With reference to the dosage form, the immunosuppressive-activity potentiating compositions of this invention can suitably be processed into solid pharmaceutical preparations, such as tablets, granules, powders and capsules, or liquid pharmaceutical preparations, such as injections and solutions for oral administration, if any, by the known procedures. In order to produce such pharmaceutical preparations, there may suitably be employed conventionally utilized excipients, binders, disintegrating agents, dispersants, reabsorption promoters, buffers, surfactants, solubilizers, preservatives, emulsifiers, isotonizing agents, stablizers and pH regulating agents as well as miscellaneous various additives.

The immunosuppressive-activity potentiating compositions based on the Present Compounds can be used as an immunosuppressive-activity potentiating composition for mammals, such as humans, dogs, rabbits, cattle, horses, monkeys, cats and sheep.

When the Present Compounds are utilized as an immunosuppressive-activity potentiating composition for humans, their doses vary depending upon the kind of the compounds, the age, body weight, sex and symptoms of patients, the dosage form, etc., and the compounds can desirably be administered to human adults at a dose in the range of about 0.5 to 200 mg once a day, preferably about 2 to 50 mg, in the case of injectable solutions, and at a dose in the range of about 5 to 2,000 mg several times a day, preferably about 20 to 500 mg, in the case of preparations for oral administration.

Described below are the experiment example and formulation examples to illustrate this invention in more detail, while the experiment example is given to clarify the effect of the present invention. This invention is not understood to be limited by these examples, wherein FIG. 1 is a graph showing numerical ratings of the results of histopathological examination after lung transplantation.

Experiment Example

Experimental materials and method:

1. Animals

Brown Norway (BN) strain rats were used as a donor, while Lewis (LEW) strain rats were utilized as a recipient.

2. Grouping

In accordance with the type and dose of drugs applied and the route of administration, the above animals were divided into groups, with the groups being named in the following:

Group treated through oral administration of a base; "Control Group".

Group treated through intravenous injection of cyclosporine A (2.5 mg/kg/day) (positive control); "Cs-A (2.5 mg) Group".

Group treated through intravenous injection of cyclosporine A (1.25 mg/kg/day); "Cs-A (1.25 mg) Group".

Group treated through intraperitoneal, consecutive trace-amount application of EPC-K (5 mg/kg/day); "EPC-K Group".

Group concomitantly treated through intraperitoneal, consecutive trace-amount application of EPC-K (5 mg/kg/day) and intravenous injection of cyclosporine A (1.25 mg/kg/day); "(EPC-K+Cs-A) Group".

3. Method of Administration of Drugs

Cyclosporine A was given through intramuscular injection (1.25 mg/kg/day and 2.5 mg/kg/day) as from the day after the surgical operation in the ordinary manner.

EPC-K was given through intraperitoneal, consecutive trace-amount application by use of a small-sized consecutive trace-amount application device (Osmic Minipump, manufactured by Alzet Co.) having a 6.75% aqueous EPC-K solution contained therein, as inserted into the abdominal cavity.

4. Lung Transplantation

In accordance with the conventional procedure, left-lung transplantation was conducted from a BN strain rat (RTln) to a LEW strain rat (RTl).

5. Postoperative Course Observation through X-ray Photography After Lung Transplantation Observation of the postoperative course was conducted by taking X-ray photographs every 24 hours.

6. Histopathological Examination of Acute Rejection After Lung Transplantation

The rats were sacrificed on Day 7 after lung transplantation and histopathological examination of acute rejection was conducted in accordance with the below-described criterion as proposed by Samuel et al. (A, Samuel et al., The Journal of Transplantation, vol. 9 (60, 593–601 (1990)): Criterion;

Grade 0; No acute rejection

Grade 1; Extremely slight acute rejection

Grade 2; Slight acute rejection

Grade 3; Moderate acute rejection

Grade 4; Severe acute rejection

7. Results:

Shown in FIG. 1 are the results of histopathological examination of acute rejection on Day 7 after lung transplantation. As is evident from FIG. 1, the histopathological examination results were rated at 4±0 (means ±S.D.) for the control group (6 animals), 3.38±0.26 (for the EPC-K group (6 animals) and 3.83±0.41 for the Cs-A (1.25 mg) group, with no significant difference being noted among them. However, the same examination was rated at 2.75±0.52 for the positive control of the Cs-A (2.5 mg) Group and 2.25±0.27 for the (EPC-K+Cs-A (1.25 mg)) Group (6 animals), indicating that EPC-K can achieve significant suppression of acute rejection on Day 7 after lung transplantation.

The above results demonstrated that EPC-K is useful as an immunosuppressive-activity potentiating composition.

Formulation Example 1

Pharmaceutical preparation for internal use:

EPC-K 100 mg

Lactose 75 mg

Starch 20 mg

Polyethylene glycol 6000 5 mg

The above-described ingredients are mixed and compressed into a tablet by the conventional procedure. Sugar coating can be provided to the coating, if necessary.

Formulation Example 2

Injectable solution:

EPC-K 200 mg

Mannitol 5.0 g

1N-Sodium hydroxide Appropriate amount (pH 6.5)

Distilled water To make the total up to 100 ml

The above-described ingredients are brought into a solution, which is then sterile filtered. The filtrate is filled sterile in 5-ml portions into glass ampoules, followed by fusion to prepare an injectable solution.

What is claimed:

1. A method of suppressing the immune activity of a subject in need thereof, comprising administering to the subject an amount effective for suppressing immune activity of a phosphoric acid diester compound that exhibits immunosuppressive activity and is represented by the formula I:

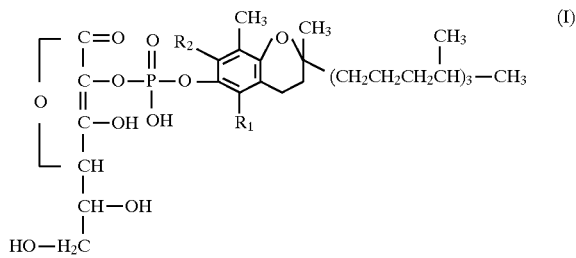

wherein $R_1$ and $R_2$ are the same or different and represent individually a hydrogen atom or methyl group, or a pharmacologically acceptable salt thereof.

2. The method of claim 1, wherein a second substance exhibiting immunosuppressive activity is administered to the subject.

3. The method of claim 2, wherein the second substance exhibiting immunosuppressive activity is a cyclosporine.

4. The method of claim 1, wherein the subject has undergone organ transplant surgery.

5. The method of claim 1, wherein the compound of formula I or its salt is administered by injection in an amount in the range of about 0.5 to 200 mg.

6. The method of claim 5, wherein the amount is about 2 to 50 mg.

7. The method of claim 1, wherein the compound of formula I is administered orally in an amount in the range of about 5 to 2000 mg.

8. The method of claim 7, wherein the amount is about 20 to 500 mg.

9. The method of claim 1, wherein the compound is administered to the subject by injection or drip.

* * * * *